United States Patent
Oku et al.

[11] Patent Number: 5,514,830
[45] Date of Patent: May 7, 1996

[54] PROCESS FOR PRODUCING NITRILE

[75] Inventors: Masayuki Oku, Naga; Yoshiaki Fujikura, Utsunomiya, both of Japan

[73] Assignee: Kao Corporation, Tokyo, Japan

[21] Appl. No.: 426,129

[22] Filed: Apr. 21, 1995

Related U.S. Application Data

[62] Division of Ser. No. 396,586, Mar. 1, 1995, Pat. No. 5,457,222, which is a continuation of Ser. No. 30,009, Mar. 25, 1993, abandoned.

[30] Foreign Application Priority Data

Jul. 25, 1991 [JP] Japan .................................. 3-186227

[51] Int. Cl.⁶ .................................................. C07C 253/00
[52] U.S. Cl. ............................................................. 558/314
[58] Field of Search ............................................... 558/314

[56] References Cited

U.S. PATENT DOCUMENTS

| | | | |
|---|---|---|---|
| 4,288,385 | 9/1981 | Lutz et al. | 558/314 X |
| 4,808,746 | 2/1989 | Nishimura et al. | 558/314 |
| 5,097,058 | 3/1992 | Cannata et al. | 558/314 |

FOREIGN PATENT DOCUMENTS

| | | | |
|---|---|---|---|
| 0550762 | 7/1993 | European Pat. Off. | 558/314 |
| 1018187 | 1/1966 | United Kingdom | 558/314 |

OTHER PUBLICATIONS

CRC Handbook of Chemistry and Physics, 60th ed., 1980, Weast et al, pp. D–13, D–26, D–6, D–36, D–34.

*Primary Examiner*—Joseph Paul Brust
*Attorney, Agent, or Firm*—Oblon, Spivak, McClelland, Maier & Neustadt

[57] ABSTRACT

The present invention provides a process for producing a nitrile represented by the general formula (1):

$$RC\equiv N \qquad (1)$$

wherein R is alkyl, alkenyl, aralkyl or aryl, each may have a substituent, characterized by heating an aldoxime represented by the general formula (2):

$$RCH=NOH \qquad (2)$$

wherein R is as defined above, in the presence of one or more catalysts selected from hydroxides of alkali metals, alcoholates of alkali metals, hydroxides of alkaline earth metals and alcoholates of alkaline earth metals, and distilling off water formed in the course of the reaction from the reaction system. The process according to the present invention can produce a nitrile which is useful as a perfume or as a starting material for the organic synthesis of perfumes, medicines and so on in high yields and advantageously from the viewpoint of production economy.

14 Claims, No Drawings

PROCESS FOR PRODUCING NITRILE

The present application is a divisional of application Ser. No. 08/396,586, filed Mar. 1, 1995, U.S. Pat. No. 5,457,222, which is a continuation of application Ser. No. 08/030,009, filed Mar. 25, 1993, abandoned, which is a U.S. national stage application of PCT/JP92/00928, filed Jul. 21, 1992.

TECHNICAL FIELD

This invention relates to a process for producing, in high yields and with ease, a nitrile which is useful as a perfume or as a starting material in the synthesis of perfumes, medicines and so on.

BACKGROUND ART

Several processes are known for obtaining a nitrile from an aldoxime by the use of a dehydrating agent. Typical processes include: (A) a process where an aldoxime is allowed to react with an acid anhydride such as acetic anhydride for dehydration, and (B) a process where an aldoxime is dehydrated with a phosphonitrilic chloride trimer (hexachlorocyclotriphosphazene).

However, process (A) involves disadvantages of high cost of starting material because acetic anhydride is needed in an equimolar amount or more with respect to the amount of aldoxime, and in addition, disposal of waste acetic acid finally produced from the acetic anhydride is required. On the other hand, when process (B) is adopted, phosphonitrilic chloride must be used in an equimolar amount or more with respect to the amount of aldoxime, which means a high cost of starting material, and moreover, waste disposal is even more costly compared to the process utilizing acetic anhydride.

In order to avoid these disadvantages, a process utilizing an acid such as sulfuric acid as a dehydrating agent has been reported (Japanese patent publication kokoku No. 59144/1990). This process is superior to the above-mentioned process in respect of only a catalytic amount of acid and reduced amounts of wastes. But this process is still defective because of the limited application of the process. In detail, yield of 80% or more is assured to obtain a nitrile from an aromatic oxime, a reduced yield of 70% from an aliphatic oxime, and a very low yield of 12% from a terpene oxime, which indicates unsuitableness in the wide-range practice.

Accordingly, an object of this invention is to provide a process for producing a nitrile in high yields and at a remarkably advantageous production cost.

DISCLOSURE OF THE INVENTION

According to the present invention, there is provided a process for producing a nitrile represented by the general formula (1):

wherein R is alkyl, alkenyl, aralkyl or aryl, each may have a substituent, characterizing by heating an aldoxime represented by the general formula (2):

wherein R is as defined above, in the presence of one or more catalysts selected from hydroxides of alkali metals, alcoholates of alkali metals, hydroxides of alkaline earth metals and alcoholates of alkaline earth metals, and distilling off water formed in the course of the reaction from the reaction system.

BEST MODE FOR CARRYING OUT THE INVENTION

This invention will now be described in detail.

This invention is shown by the following reaction scheme:

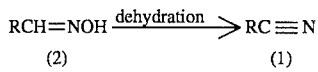

wherein R has the same meaning as defined above.

In other words, according to the present invention, a nitrile of the general formula (1) is prepared by heating an aldoxime represented by the general formula (2) in the presence of at least one catalyst selected from hydroxides of alkali metals, alcoholates of alkali metals, hydroxides of alkaline earth metals and alcoholates of alkaline earth metals, and distilling off water formed in the course of the reaction from the reaction system.

Preferable group R in formulas (1) and (2) above are those having 3 to 20 carbon atoms. Among them, examples of alkyl include heptyl, nonyl, undecyl, lauryl and myristyl. Alkenyl groups may contain two or more double bonds, and exemplary alkenyls are led by 2,6-dimethyl-1,5-diheptadienyl group, 2,6-dimethyl-5-heptenyl group and the like. Examples of aralkyl include 2-phenethyl and 2-styryl, examples of aryl include phenyl, methylphenyl and dimethylphenyl.

Examples of substituents which may be contained in these groups include cyano, hydroxyl, alkoxyl, nitro, alkoxycarbonyl, amide and a halogen atom.

Aldoxime (2) which is a starting compound and is useful in the present invention can be obtained, for example, from the reaction between a corresponding aldehyde and an inorganic salt of hydroxyl amine by a conventional method.

Examples of the catalyst which are useful in the reaction of the present invention include hydroxides of alkali metals, alcoholates of alkali metals, carbonates of alkali metals, bicarbonates of alkali metals, hydroxides of alkaline earth metals, alcoholates of alkaline earth metals, carbonates of alkaline earth metals and bicarbonates of alkaline earth metals. They may be used singly or in combination as desired. In detail, sodium hydroxide, potassium hydroxide, lithium hydroxide, calcium hydroxide, barium hydroxide, magnesium hydroxide, sodium methoxide, sodium ethoxide, potassium propoxide, potassium isopropoxide, lithium butoxide, sodium carbonate, potassium carbonate, lithium carbonate, calcium carbonate, magnesium carbonate, sodium hydrogencarbonate, potassium hydrogencarbonate and lithium hydrogencarbonate and the like can be used singly or in combination of two or more.

Among these catalysts, preferable ones are hydroxides of alkali metals, alcoholates of alkali metals, hydroxides of alkaline earth metals and alcoholates of alkaline earth metals in view of the yield, and when production cost is further considered, sodium hydroxide and potassium hydroxide are most preferred.

In the present invention, the preferable amount of catalyst is from 0.1 to 50% by weight, and especially, 0.1 to 5% by weight in total with respect to the starting aldoxime (2). An amount less than 0.1% by weight will result in a low yield of nitrile, and an amount in excess of 50% by weight can no more improve the effect obtainable from the use of catalysts in an amount of 50% by weight or less.

Preferable temperature range for obtaining nitrile (1) from aldoxime (2) according to this invention is from 80° to 200° C.

No particular limitation is imposed as to the means for distilling off water formed in the course of the reaction from the reaction system, and mention may be given to azeotropic distillation by the use of a solvent which can form an azeotropic mixture with water, and distillation by evaporation under reduced pressure of the reaction system, both promise an effective production.

Examples of solvents which can form an azeotropic mixture with water include benzene, toluene, xylene, chlorobenzene and heptane.

Preferable process for distilling off water by evaporation under reduced pressure is such that aldoxime (2) is supplied to a mixture of a solvent of high-boiling point and one or more of the aforementioned catalysts under reduced pressure at a reaction temperature, followed by distilling off the produced water successively. Here, examples of high-boiling point solvent include those which have a higher boiling point than the reaction product, nitrile (1), such as liquid paraffin and alkylbenzene.

In the present invention, the reaction for obtaining nitrile (1) from aldoxime (2) preferably proceeds, in general, under atmospheric pressure when an azeotropic distillation by the use of the above-mentioned azeotropic solvents is adopted for removing water. On the other hand, when distillation of water by evaporation under reduced pressure by the addition of a high-boiling point solvent is adopted, the reaction preferably proceeds under 200 torr or less, more preferably 60 torr or less, in general.

The thus obtained crude nitrile is purified by evaporation, column chromatography or the like to isolate the target compound, nitrile (1).

EXAMPLES

This invention will now be described in detail by way of examples, which however, should not be construed as limiting the invention thereto.

Example 1

Into a 200 ml four-neck flask equipped with a stirrer, a thermometer and a Deanstark dehydrating apparatus, 50 g of 3,7-dimethyl-6-octenoxime, 2 g of potassium hydroxide and 25 ml of toluene were charged. While the water formed is azeotropically distilled off together with toluene under reflux, stirring was continued for 2 hours at 126° C., followed by cooling down to 30°–40° C. Subsequently, the content was neutralized with acetic acid, toluene was distilled off and evaporation was performed to obtain 44.0 g of a fraction of distillate (90°˙C./5 mmHg). Analysis of the obtained fraction revealed the production of 3,7-dimethyl-6-octenonitrile in the purity of 94.5%, yield of 93%, conversion of 99% and selectivity of 94%.

Here, the conversion and selectivity are respectively defined as follows:

$$\text{Conversion (\%)} = \frac{\text{(Weight of charged oxime)} - \text{(Weight of recovered oxime)}}{\text{(Weight of charged oxime)}} \times 100$$

$$\text{Selectivity (\%)} = \frac{\text{(Mols of produced nitrile)}}{\text{(Mols of converted oxime)}} \times 100$$

Example 2

Into a 200 ml four-neck flask equipped with a stirrer, a thermometer and a Deanstark dehydrating apparatus, 50 g of 3,7-dimethyl-6-octenoxime, 5 g of sodium hydroxide and 25 ml of toluene were charged. While the water formed is azeotropically distilled off together with toluene under reflux, stirring was continued for 2 hours at 125° C., followed by cooling down to 30°–40° C. Subsequently, the content was neutralized with acetic acid, toluene was distilled off and evaporation was performed to obtain 41.2 g of a fraction of distillate (90° C./5 mmHg). Analysis of the obtained fraction revealed the production of 3,7-dimethyl-6-octenonitrile in the purity of 95.5%, yield of 88%, conversion of 99% and selectivity of 89%.

Example 3

Into a 200 ml four-neck flask equipped with a stirrer, a thermometer and a Deanstark dehydrating apparatus, 50 g of 3,7-dimethyl-2,6-octadienoxime, 5 g of potassium hydroxide and 25 ml of toluene were charged. While the water formed is azeotropically distilled off together with toluene under reflux, stirring was continued for 2 hours at 126° C., followed by cooling down to 30°–40° C. Subsequently, the content was neutralized with acetic acid, toluene was distilled off and evaporation was performed to obtain 46.0 g of a fraction of distillate (79° C./2 mmHg). Analysis of the obtained fraction revealed the production of 3,7-dimethyl-2,6-octadienonitrile in the purity of 94.5%, yield of 90%, conversion of 99% and selectivity of 91%.

Example 4

Into a 200 ml four-neck flask equipped with a stirrer, a thermometer and a Deanstark dehydrating apparatus, 50 g of heptanoxime, 2 g of potassium hydroxide and 25 ml of toluene were charged. While the water formed is azeotropically distilled off together with toluene under reflux, stirring was continued for 2 hours at 120° C., followed by cooling down to 30°–40° C. Subsequently, the content was neutralized with acetic acid, toluene was distilled off and evaporation was performed to obtain 36.8 g of a fraction of distillate (90° C./15 mmHg). Analysis of the obtained fraction revealed the production of heptanonitrile in the purity of 98.7%, yield of 83%, conversion of 97% and selectivity of 86.7%.

Comparative Example 1

Into a 200 ml four-neck flask equipped with a stirrer, a thermometer and a Deanstark dehydrating apparatus, 50 g of 3,7-dimethyl-6-octenoxime, 2.5 g of sulfuric acid and 25 ml of toluene were charged. Under reflux, stirring was performed for 2 hours at 124° C., followed by cooling down to 30°–40° C. Subsequently, the content was neutralized with sodium hydrogencarbonate, toluene was distilled off and evaporation was conducted to obtain 36.4 g of a fraction of distillate (90° C./5 mmHg). Analysis of the obtained fraction revealed the production of 3,7-dimethyl-6-octenonitrile in the purity of 7.1%, yield of 6%, conversion of 46.6% and selectivity of 12%. 26.7 g of unreacted oxime was recovered.

Examples 5–8

Procedure of Example 1 was followed using 1 g of a compound shown in Table 1 as a basic catalyst and 50 g of a starting aldoxime as shown in Table 1 to prepare a nitrile. The obtained nitriles, yields, conversions and selectivities are also shown in Table 1.

TABLE 1

| Ex. No. | Starting Aldoxime | Catalyst | Produced Nitrile | a) | b) | c) |
|---|---|---|---|---|---|---|
| 5 | 3,7-dimethyl-6-octenoxime | sodium methoxide | 3,7-dimethyl-6-octenonitrile | 99 | 77 | 78 |
| 6 | benzoxime | potassium hydroxide | benzonitrile | 99 | 75 | 76 |
| 7 | 3-phenyl-propanoxime | potassium hydroxide | 3-phenyl-propanoxime | 99 | 85 | 86 |
| 8 | 3-phenyl-2-propenoxime | potasuium hydroxide | 3-phenyl-2-propenoxime | 99 | 80 | 81 | a): Yield (%)
b): Conversion (%)
c): Selectivity (%)

Example 9

Into a 300 ml flask equipped with a thermometer, stirrer, charging tube and a distillating tube, 30 g of liquid paraffin and 6 g of KOH were placed, stirred, heated at 110°–120° C., and the pressure was controlled to be 50 torr. Subsequently, 3,7-dimethyl-2,6-octadienoxime was supplied at a rate of 100 g/hour over 3 hours, and aged for 1 hour under the same conditions to obtain 258 g of an oil distillate together with a small amount of water. Analysis of this fraction revealed that 3,7-dimethyl-2,6-octadienonitrile was produced in the purity of 93.5% and yield of 90.0%.

INDUSTRIAL APPLICABILITY

According to the process of the present invention, a nitrile which is useful as a perfume or as a starting material in the synthesis of perfumes, medicines and so on can be obtained in high yields and at a remarkably advantageous production cost. Wide range of application of the present process, therefore, is expected in various fields of the perfume manufacture, medicine manufacture and the like.

We claim:

1. A process for producing a nitrile represented by formula (1):

$$RC\equiv N \quad (1)$$

wherein R is alkyl, alkenyl, aralkyl, 2-styryl or aryl, each of which is optionally substituted by one or more radicals selected from the group consisting of cyano, hydroxyl, alkoxyl, nitro, alkoxycarbonyl, amide and halogen, comprising the steps of:

(a) heating an aldoxime represented by formula (2):

$$RCH=NOH \quad (2)$$

wherein R is as defined above, in the presence of one or more catalysts selected from the group consisting of hydroxides of alkali metals, alcoholates of alkali metals having from 1 to 4 carbon atoms, hydroxides of alkaline earth metals and alcoholates of alkaline earth metals having from 1 to 4 carbon atoms; and (b) evaporating off the water formed during the course of the reaction from the reaction system under a reduced pressure of 200 torr or less.

2. The process of claim 1, wherein said heating is conducted at a temperature of 80°–200° C.

3. The process of claim 1, wherein said catalyst is present in an amount of 0.1 to 50% by weight of said aldoxime.

4. The process of claim 1, wherein said heating is conducted in a high-boiling solvent.

5. The process of claim 1, wherein said reduced pressure is 60 torr or less.

6. The process of claim 4, wherein said solvent has a higher boiling point than said nitrile.

7. The process of claim 6, wherein said solvent is selected from the group consisting of liquid paraffin and alkylbenzenes.

8. A process for producing a nitrile represented by formula (1):

$$RC\equiv N \quad (1)$$

wherein R is alkyl, alkenyl, aralkyl, 2-styryl or aryl, each of which is optionally substituted by one or more radicals selected from the group consisting of cyano, hydroxyl, alkoxyl, nitro, alkoxycarbonyl, amide and halogen, comprising the steps of:

(a) heating an aldoxime represented by formula (2):

$$RCH=NOH \quad (2)$$

wherein R is as defined above, in a mixture of a high-boiling solvent and one or more catalysts selected from the group consisting of hydroxides of alkali metals, alcoholates of alkali metals having from 1 to 4 carbon atoms, hydroxides of alkaline earth metals and alcoholates of alkaline earth metals having from 1 to 4 carbon atoms, under reduced pressure; and simultaneously, (b) evaporating off the water formed during the course of the reaction from the reaction system.

9. The process of claim 8, wherein said solvent has a higher boiling point than said nitrile.

10. The process of claim 9, wherein said solvent is selected from the group consisting of liquid paraffin and alkylbenzenes.

11. The process of claim 8, wherein said heating is conducted at a reaction temperature is 80°–200° C.

12. The process of claim 8, wherein said catalyst is present in an amount of 0.1 to 50% by weight of said aldoxime.

13. The process of claim 8, wherein said evaporating is conducted at a reduced pressure of 200 torr or less.

14. The process of claim 11, wherein said evaporating is conducted at a reduced pressure of 200 torr or less.

* * * * *